United States Patent [19]

Sinnreich

[11] Patent Number: 5,032,403

[45] Date of Patent: Jul. 16, 1991

[54] MULTILAYER PLASTER

[75] Inventor: Joel Sinnreich, Basel, Switzerland

[73] Assignee: Ciba-Geigy Corporation, Ardsley, N.Y.

[21] Appl. No.: 387,322

[22] Filed: Jul. 28, 1989

[30] Foreign Application Priority Data

Aug. 2, 1988 [CH] Switzerland .................. 2920/88

[51] Int. Cl.⁵ .................. A61F 13/02; A61L 15/06
[52] U.S. Cl. .................. 424/448; 424/449; 424/443; 424/444; 424/78; 514/946; 514/947
[58] Field of Search .............. 424/448, 449, 443, 444, 424/445; 514/946, 947

[56] References Cited

U.S. PATENT DOCUMENTS

| | | | |
|---|---|---|---|
| 4,440,770 | 4/1984 | Mochida et al. | 424/258 |
| 4,560,553 | 12/1985 | Zupan | 424/78 |
| 4,623,346 | 11/1986 | von Bittera et al. | 604/896 |
| 4,627,852 | 12/1986 | von Bittera et al. | 604/897 |
| 4,668,232 | 5/1987 | Cordes | 604/897 |
| 4,699,792 | 10/1987 | Nick et al. | 424/446 |
| 4,776,850 | 10/1988 | Guse et al. | 604/304 |

*Primary Examiner*—Thurman Page
*Assistant Examiner*—James M. Spear
*Attorney, Agent, or Firm*—Irving M. Fishman; JoAnn Villamizar

[57] ABSTRACT

The invention relates to a transdermal therapeutic system in the form of a multilayer plaster for the administration of active substances which are able to permeate, in the form of a matrix system containing at least three layers:

(a) a covering layer which is impermeable for the constituents of the reservoir b);
(b) a reservoir layer which is able to deliver active substance and which consists of optionally cross-linked block copolymer based on styrene, alkadienes and optionally alkenes mixed with adhesive polymers and is optionally provided with an additional adhesive membrane layer and contains at least one active substance capable of skin permeation, at least one agent promoting the skin permeability of active substances and optionally further pharmaceutical auxiliaries, and
(c) a protective film which can be pulled off the reservoir layer.

9 Claims, No Drawings

MULTILAYER PLASTER

The invention relates to a multilayer plaster for the transdermal administration of active substances which are able to permeate through the skin, to a process for the preparation of this plaster, and to the therapeutic use thereof for the prevention and treatment of various conditions and diseases.

Topical application of systemic active substances with creams, ointments, pastes, lotions etc. can in contrast to other parenteral administration forms, such as intravenously, be carried out by almost all patients themselves and is also painless. Compared with oral administration with tablets or capsules, topical application is a suitable alternative when breakdown of the active substance on passage through the liver makes high dosages, with an increased risk of side effects, necessary.

It is known that the permeability of systemic active substances can be increased considerably with certain agents which promote skin penetration thereof ("skin-penetrating agents or penetrating agents, flux enhancers"), e.g. with dimethyl sulfoxide, dimethylformamide or methyl n-dodecyl sulfoxide, see U.S. Pat. No. 3,257,864, or 1-n-dodecylazacyclohexan-2-one, see U.S. Pat. No. 4,316,893. These auxiliaries are also known as agents which particularly strongly increase the permeability of many systemic active substances. The suitability of eucalyptol and mixtures of eucalyptol with other skin-penetrating agents, especially mixed with N-methyl-2-pyrrolidone in the ratio 1:1, to increase the permeability of systemic active substances in topical products such as creams, ointments, pastes and lotions etc is described in European Patent Application No. 69 385.

The said topical preparations can, however, be applied for only a short time, must often be renewed and in general, because the distribution thereof on the skin is non-uniform, allow only inexact dosage of the active substance. As an alternative to application with preparations of these types, application of systemic active substances with transdermal therapeutic systems is especially suitable when continuous release of the active substance component with controlled dosage is intended over a prolonged period.

However, because of the low permeability of the skin, especially of the outer horny skin layer, the systemic active substances to be administered transdermally with therapeutic systems of this type must comply with the following profile of requirements:

1. Despite the barrier function of the outer horny layer they must be able to permeate through skin sufficiently to gain access to the circulating blood;
2. They must be well tolerated by the skin;
3. They must additionally be suitable for long-term prophylactic or therapeutic use or for replacement therapy (see also H. Asche, Pharma International 4 (P), 1984, page 162).

This strict profile of requirements limits the choice of the available active substances which can be administered transdermally, so that corresponding therapeutic systems have hitherto found use in therapy with only a few active substances, e.g. with the active substances scopolamine, nitroglycerin, oestradiol or clonidine.

There are likewise problems with the use of the said skin-penetrating agents in transdermal therapeutic systems. Because of their high dissolving power for polymeric organic material, these may alter disadvantageously the maintenance of shape fo the constituents of the system. In the matrix system which are straightforward to produce industrially, the matrix layer becomes detached from the covering layer or from any adhesive layer which is present. Occasionally, the adhesive action of the matrix layer unintentionally becomes so strong that it is possible to remove the plaster again only with the application of increased force. The present invention has the object of producing a form for the administration of systemic active substances in the form of a transdermal therapeutic matrix system with improved stability and delivery properties. This object is achieved by the present invention which relates to a particularly advantageous transdermal therapeutic system in the form of a multilayer plaster with a matrix layer composed of optionally crosslinked styrene block copolymers mixed with alkane or alkadiene homopolymers and particularly beneficial delivery properties, maintenance of shape and adhesive action.

The multilayer plaster has the following constituents:

(a) a covering layer which is impermeable to the constituents of the reservoir layer (b);

(b) a reservoir layer which is able to deliver active substance and which consists of optionally crosslinked block copolymer based on styrene, alkadienes and optionally alkenes mixed with adhesive polymers and is optionally provided with an additional adhesive membrane layer and contains at least one active substance capable of skin permeation, at least one agent promoting skin permeability of active substances and optionally further pharmaceutical auxiliaries, and (c) a protective film which can be pulled off the reservoir layer.

The terms and definitions used hereinbefore and hereinafter preferably have the following meanings within the scope of the description of the present invention:

The covering layer (a) consists of a polymeric material or a combination of polymeric materials, which must be impermeable to the constituents of the reservoir layer (b), especially liquid constituents of the formulation. It acts as the outer protective layer of the system. It is possible to use for the production of this covering layer high or low density polymers, which are optionally coated with metal foil such as aluminum foil, such as polyethylene, polypropylene, polyvinyl chloride, polyethylene terephthalate, cellulose acetate, vinyl acetate/vinyl chloride copolymers, polyacrylates, polyesters or ethylene/vinyl acetate copolymers. An impermeable flexible covering layer which adapts itself to the shape of the relevant part of the body to which the plaster is applied is preferred.

The reservoir layer (b) is located between the covering layer (a) and the protective film (c) and consists of a mixture of block copolymers which are tolerated by skin, optionally crosslinked and based on styrene, alkadienes and optionally alkenes mixed with adhesive polymers. The reservoir layer (b) contains an active substance which is able to permeate through the skin, or combinations thereof, at least one agent promoting the skin permeability of active substances (penetrating agents) and optionally pharmaceutical auxiliaries. The reservoir layer (b) can additionally contain a permeable and adhesive membrane for controlling the amount delivered per unit time of the active substance which is to be administered from the system onto the skin and/or an additional adhesive layer to improve the adhesion properties.

Block copolymers based on styrene, alkadienes and optionally alkenes are known and belong to the group of synthetic rubbers which have an irregular arrangement of the double bonds in the carbon chain and which are formed by copolymerization of alkadienes with styrene or by polymerization of alkadienes and alkenes with styrene. The copolymerization can take place, in particular, between $C_4$–$C_6$alkadienes, e.g. butadiene or isoprene, and styrene or between the said $C_4$–$C_6$alkadienes and $C_2$–$C_4$-alkenes, e.g. ethylene or propylene, and styrene. Preferred block copolymers have an alkadiene monomer content or an alkadiene/alkene monomer content of at least 40%, preferably 50%. Particularly preferred block copolymers are those based on styrene, alkadienes and optionally alkenes and which are marketed as synthetic rubbers by Shell under the tradenames CARIFLEX and KRATON.

The said block copolymers can be crosslinked by addition of customary crosslinkers such as sulfur or additives able to release sulfur, such as dimorpholyl disulfide, 2-morpholinodithiobenzothiazole, caprolactam disulfide or dipentamethylenethiuram tetrasulfide (vulcanizing agents), optionally with the addition of vulcanization accelerators, especially of the type of sulfenamides, triazines, guanidines, thiurams, dithiocarbamates, xanthates, aldehyde/amine condensation products, amines or thioureas, using customary vulcanization processes, preferably at temperatures below 100° C. In place of the use of vulcanizing agents, the block copolymers can be crosslinked wholly or partially, on the surface or throughout, preferably by exposure to high-energy radiation, optionally with the addition of photosensitizers, e.g. with gamma radiation, e.g. from $^{60}$Co sources, electronic radiation or ultraviolet radiation in a wavelength range of about 200 to 400 nm which is generated in mercury vapour lamps with high-pressure or low-pressure discharge.

Particularly preferred are butadiene/styrene block copolymers and ethylene/butadiene/styrene block polymers, especially of the type of KRATON, e.g. KRATON GX 1657, or CARIFLEX e.g. CARIFLEX TR 107, these latter being wholly or partially crosslinked by exposure to high-energy radiation, e.g. ultraviolet radiation.

There is admixture of adhesive polymers which are permeable both to the active substances and to the penetrating agent and have sufficient adhesiveness in addition to being tolerated by the skin.

Examples of adhesive polymers of this type are silicone rubber (silicones), e.g. linear polysiloxanes, in which the silicon atoms in the siloxane chain are substituted by two identical or different alkyl, e.g. methyl or ethyl, aryl, e.g. phenyl, alkenyl, e.g. vinyl or allyl, alkylaryl, e.g. tolyl or xylyl, or aralkyl, e.g. benzyl, radicals, and the terminal silicon atoms are substituted by three of the said organic radicals. The preparation of these silicones is described in U.S. Pat. Nos. 2,541,137, 2,723,966, 2,863,846, 2,890,188, 2,927,907, 3,002,951 and 3,035,016, preference being given to the silicones vulcanizable at room temperature.

Adhesive polymers are furthermore hydrophilic polymers of monoesters of unsaturated carboxylic acids such as acrylic acid or methacrylic acid, e.g. the poly(-hydroxyethyl acrylates) or poly(hydroxyethyl methacrylates) thereof, whose preparation is described in U.S. Pat. Nos. 2,976,576 and 3,220,960, as well as copolymers of water-soluble aliphatic or cyclic vinylamides, e.g. poly-N-vinyl-methylacetamide, -ethylacetamide, -methylpropionamide, -ethylpropionamide, -methylisobutyramide, -2-pyrrolidone, -2-piperidone, -epsilon-caprolactam, -5-methyl-2-pyrrolidone or -3-methyl-2-pyrrolidone, especially poly-N-vinylpyrrolidone with a mean molecular mass of about 10,000-360,000, with water-soluble polyvinyl acetate or polyvinyl alcohol with varying acetate content, e.g. polyvinyl acetate with a molecular mass of about 5,000 to 400,000 or polyvinyl alcohol with a degree of hydrolysis of about 85-98% and a degree of polymerization of about 500-2,500.

Preferably admixed are alkene or alkadiene homopolymers which increase the elasticity and tack of the reservoir layer (b). Examples of homopolymers of this type are high-density or low-density polyethylene, polypropylene, polybutadiene, e.g. butadiene sodium ("numbered Buna" of type 32 or 85) or cis-1,4-polybutadiene, polyisoprene or, in particular, polyisobutylene with an average molecular weight range from about $1.0 \times 10^3$ to $5.0 \times 10^4$, e.g. polyisobutylene with the name OPPANOL (BASF), e.g. OPPANOL B-10. It is also possible, to improve the tack, to use the resins known in the specialist literature, e.g. colophony.

The reservoir layer (b), which contains the active substance which is able to permeate, e.g. progesterone, and a skin-penetrating agent, e.g. eucalyptol combined with N-methyl-2-pyrrolidone, is able to adhere to the skin sufficiently well for the plaster to remain fixed there for at least one day and then to be removed without the application of increased force. In addition, the plaster is distinguished by high efficiency of delivery of the active substance which is to be administered, so that delivery of therapeutically effective amounts of the active substance which is to be administered transdermally is ensured. Surface crosslinking, e.g. brief irradiation with high-energy light, is a possible way of conferring on the reservoir layer (b) the property of a permeable membrane, which controls the permeability for the active substance and the penetrating agent.

The reservoir layer (b) can, moreover, be provided with an additional permeable membrane which has the required permeability for the active substance and the penetrating agent. This layer additionally controls the rate of delivery of the penetrating agent and, where appropriate, the combination of active substances from the system onto the skin and is also called the regulating or control membrane.

The materials which can be used to produce the permeable membrane are known per se. Membrane materials of this type can be homogeneous (diffusion membranes) or have a macrostructure (porous membranes). The latter may be regarded as sponge-like structure with a perforated framework structure of polymeric material in which interconnected interstices and pores are dispersed. Membrane materials which control the rate of delivery can consist of isotropic material with a homogeneous structure or of anisotropic material with a non-homogeneous structure. Materials of these types are commercially available and can be produced in a variety of ways, e.g. as described by R.E. Kesting, Synthetic Polymer Membranes, McGraw Hill, Chapters 4 and 5, 1971, J. D. Ferry, Ultrafiltration Membranes, Chemical Review, Vol. 18, page 373, 1984.

Membrane materials with 5 to 95% by volume of voids and an effective pore size of about $1.0 \times 10^{-9}$ m to $1.0 \times 10^{-4}$ m are particularly suitable. Especially suitable are membrane materials with pore sizes below about $5.0 \times 10^{-9}$ m. For optimal results reference may be made to the state of the art and the known embodiments with known membrane materials and known design, which ensure an optimal rate of delivery of the active substance or of the combination of active substances. In particular, the membrane material must be chemically resistant to the active substance or the combination of active substances and to the penetrating agent which is used.

A list of suitable membrane materials, which should not be regarded as exhaustive, is indicated hereinafter:

Polycarbonates, e.g. linear polyesters of carbonic acid derivatives which contain carbonate groups in the polymer chain and can be prepared, for example, by reaction of dihydroxy aromatic compounds with phosgene. Materials of this type can be obtained under the tradename Lexan ® from General Electric;

Polyvinyl chlorides, e.g. the PVC which can be obtained under the tradename Geon ®121 from Goodrich;

Polyamides of the polyhexamethyleneadipamide type or those polyamides which are known under the generic name "nylon". A particularly suitable material is marketed under the tradename Nomex ® by DuPont;

Acrylic acid copolymers, e.g. those which are sold under the commercial name Dynel ® and consist of about 60% polyvinyl chloride and 40% copolymerized acrylonitrile, as well as styrene/acrylic acid copolymers and the like;

Polysulfones with diphenyl sulfone groups in the linear chain. Polymers of this type are marketed by Union Carbide under the name P-1700;

Halogenated polymers such as polyvinylidene fluorides which are marketed, for example, under the tradename Kynar ® by Pennwalt; polyvinyl fluorides which can be obtained under the tradename Tedlar ® from DuPont, as well as polyfluorohalocarbon obtainable under the tradename Aclar ® from Allied Chemical;

Polychloroethers which are marketed under the tradename Penton ® by Hercules, as well as other similar thermoplastic polymers;

Acetal polymers such as the polyformaldehyde polymers which are marketed by DuPont under the tradename Delrin ®, and the like;

Acrylic acid resins such as poly(methyl methacrylate), poly(n-butyl methacrylate) and the like;

Polyethylene and copolymers of ethylene, for example with vinyl acetate or acrylates.

Several arrangements are possible when a permeable membrane is used; the active substance and the penetrating agents are located in the matrix which is formed of block copolymer and alkene or alkadiene homopolymer between the covering layer (b) and the permeable membrane.

It is also possible, in accordance with the embodiment described in German Offenlegungsschrift No. 3,205,258, to fill the volume which is formed by the covering layer (a) and the permeable membrane only with the penetrating agent, e.g. eucalyptol, and the mixture of block copolymer and alkane or alkene homopolymer and to apply the active substance or a combination of active substances to the other side of the membrane. In this case, the membrane controls only the rate of diffusion of the penetrating agent. The active substance or the combination of active substances can also be present in a separate layer between the membrane and an additional adhesive material and, optionally or exclusively, in the additional adhesive material, which can be located on the membrane layer.

Suitable for increasing the tack are the adhesive materials which can be used in dermatology. Examples of suitable adhesive materials are adhesive formulations of acrylic acid or methacrylic acid resins, e.g. polymers of acrylic acid or methacrylic acid esterified with alcohols such as n-butanol, n-pentanol, isopentanol, 2-methylbutanol, 1-methylbutanol, 1-, 2- or 3-methylpentanol, 2-ethylbutanol, isooctanol, n-decanol or n-dodecanol, or copolymers of these acrylic acid or methacrylic acid esters with monomers containing ethylene groups, such as acrylic acid itself, methacrylic acid, acrylamide, methacrylamide, N-alkoxymethacrylamide, N-alkoxymethylmeth-acrylamide, N-tert-butylamide, itaconic acid, vinyl acetate, N-branched alkylmaleamide in which the branched alkyl group has 10–24 C atoms. Glycol diacrylates or mixtures thereof, natural or synthetic rubber such as styrene/butadiene, butyl ether, neoprene, polyisobutylene, polybutadiene and polyisoprene, polyvinyl acetate, urea/formaldehyde resins, resorcinol/formaldehyde resins, cellulose derivatives such as ethylcellulose, methylcellulose, nitrocellulose, cellulose acetate butyrate and carboxymethylcellulose as well as natural adhesives such as guar, acacia, pectin, starch, dextrin, albumin, gelatin, casein etc. It is also possible to add thickeners and stabilizers to the said adhesives.

This adhesive material can be partially or completely applied to the membrane or directly to the matrix composed of block copolymer and alkene homopolymer. When the matrix is completely covered with adhesive layer, the latter can, besides its virtual function as adhesive on the skin, additionally act as permeable membrane. Desired membrane properties, e.g. control of the rate of diffusion of the penetrating agent, can be achieved by varying the thickness and composition of the adhesive layer. The adhesive material can additionally contain the total or, preferably, a portion of the amount of the active substance which is to be administered or of the combination of active substances. It is possible, in particular, with the amount of active substance contained in the adhesive material to achieve administration of an initial high dose before the onset of the continuous administration at the desired therapeutic level controlled by the therapeutic system.

The membrane or the matrix may additionally be partially and/or discontinuously covered with adhesive material. Possible in this connection is a marginal coverage, e.g. annular coverage around the edge. The membrane can also have a patterned covering, e.g. in the form of lozenges. The membrane can be covered on the outer edge by a continuous strip of adhesive material, e.g. annular, and on the inner area with discontinuous strips so that a rhombic pattern results.

The reservoir layer contained in the plaster according to the invention contains an agent (penetrating agent) which promotes the skin-permeability of systemic active substances and which increases the permeability of the active substances through the skin so that a larger amount of active substances, based on the application area and unit time, is absorbed by the skin. The penetrating agent can additionally increase the rate at which the active substance is passed through the matrix and, where appropriate, the membrane layer. In particular, when a suitable penetrating agent is used the dosed amount of active substances per unit time necessary to maintain the therapeutic level is administered through the skin. Suitable penetrating agents can be mixed with other pharmaceutically acceptable auxiliaries. phatic or aromatic hydrocarbons with 5 to 12 C atoms, e.g. hexane, cyclohexane, isopropylbenzene and the like, cycloaliphatic or aromatic aldehydes and ketones with 4 to 10 C atoms such as cyclohexanone, acetamide, cyclic amides such as N-methyl-2-pyrrolidone or 1,3-dimethyl-2-imidazolidinone, N,N-di-lower-alkylacetamide such as N,N-dimethyl- or N,N-diethylacetamide, $C_{10}$-$C_{20}$alkanoylamides, e.g. N,N-dimethyllauroylamide, 1-n-$C_{10}$-$C_{20}$alkylazacycloheptan-2-one, e.g 1-n-dodecylazacycloheptan-2-one (Azone®, Nelson), or N-2-hydroxyethylacetamide, as well as known transport agents and/or penetrating agents such as branched and unbranched, aliphatic, cycloaliphatic and aromatic esters, N,N-di-loweralkyl sulfoxide, unsaturated oils, halogenated or nitrated aliphatic, cycloaliphatic hydrocarbons, salicylates, polyalkylene glycol silicates and mixtures thereof.

A combination of eucalyptol with one of the said penetrating agents, especially with N-methyl-2-pyrrolidone, is preferred.

The term eucalyptol embraces compositions containing about 70-100% 1,8-cineole. Compositions containing about 70-95% 1,8-cineole are also called eucalyptus oils in various pharmacopoeias (U.S.P. or Eur. Pharm.), whereas the term eucalpytol is used only for compositions containing more than 95% 1,8-cineole.

Eucalyptus oils are terpene-containing essential oils which contain eucalyptol or 1,8-cineole as main constituent (more than 70%) or as sole component and can be isolated from the leaves, roots or bark of eucalyptus plants of the species *Eucalyptus globulus* (common eucalyptus tree), *Eucalyptus maculata, Eucalyptus cladocalyx* or *Eucalyptus sideroxylon*. Eucalyptus oil can be further processed by customary purification processes, e.g. rectification, to chemically pure 1,8-cineole (content exceeding 99%). The reservoir layer (b) preferably contains this chemically pure 1,8-cineole with the additional penetrating agent N-methyl-2-pyrrolidone.

When a combination of eucalyptol, preferably in the form of chemically pure 1,8-cineole, is used with an additional penetrating agent and the absence of a membrane layer, the amount delivered and the rate of delivery (amount delivered per unit time) of the active substance contained in the reservoir layer (b), or of a combination of active substances present therein, from the reservoir layer (b) consisting of a membrane layer to the skin and the corresponding absorption (or rate of absorption) through the skin is considerably increased. Thus, in a period up to 24 hours after application of the system, substantially constant amounts of the active substance which is to be administered are delivered to the skin. Besides the active substance itself or the combination of active substances, adequate amounts of the penetrating agents contained in the system are delivered, so that the skin permeability of the active substance is enhanced and the absorption of adequate amounts of active substance is ensured.

Especially preferred is the combination of 5-9.5 parts by weight of chemically pure 1,8-cineole and, correspondingly, 5-0.5 parts by weight (based on 10 parts by weight) of N-methyl-2-pyrrolidone. Combinations of this type have the advantage over the single components N-methyl-2-pyrrolidone and 1,8-cineole that they can be processed with the polymeric material of the reservoir layer (b) to give homogeneous matrix systems which are able to deliver and have adequate adhesive property.

Particularly preferred is the combination of about 9 parts by weight of chemically pure 1,8-cineole and 1 part by weight of N-methyl-2-pyrrolidone.

The amount of active substance contained in the therapeutic system to achieve a therapeutic effect depends on many factors: inter alia on the minimum dosage amount required, on the permeability of the matrix and, where appropriate, of the membrane material with the adhesive material, and on the period of time in which the plaster is attached to the skin or the mucous membranes. Since the delivery of active substance is intended to extend over a period longer than one day there is actually no upper limit with respect to the maximum amount of active substance contained in the plaster. The minimum amount of active substance is established by the requirement that the plaster must contain adequate amounts of active substance to maintain the desired amount delivered over the intended period.

It is possible in this connection to use all pharmaceuticals which are able to permeate and which are absorbed by the area of skin provided with the plaster. Examples of pharmaceuticals of this type are antibacterial active substances such as penicillins, tetracyclines, oxytetracyclines, chlorotetracyclines, chloramphenicol or sulfonamides, sedatives and/or hypnotics such as pentabarbital sodium, phenobarbital, secobarbital sodium, codeine, alpha-bromoisovalerylurea, carbromal or sodium phenobarbital, psychostimulants such as 3-(2-aminopropyl)indoleacetate or 3-(2-aminobutyl)indoleacetate, antihypertensives such as reserpine, tranquillizers such as chlorpromazine hydrochloride or thiopropazate hydrochloride, hormones such as adrenocorticosteroids, e.g. (6α-methylprednisolen, androgenic steroids, e.g. methyltestosterone and fluoxymesterone, oestrogenic steroids, e.g. oestrone, 17β-oestradiol and ethinyloestradiol, progesterone or norethindrone, combinations of oestrogens with synthetic gestagens, e.g. 17β-oestradiol with norethisterone 17-acetate, antipyretics such as acetylsalicylic acid, morphine and other analgesics based on morphine, vasodilating agents, e.g. nitroglycerine or isosorbide dinitrate, cardiac glycosides such as digitoxin or ouabin, beta-blockers such as propanolol, oxprenolol or metoprolol, anticholinergics such as atropine, methscopolamine bromide, scopolamine, hyoscyamine or methscopolamine combined with phenobarbital, antimalarials such as 4-aminoquinolines, 9-aminoquinolines or pyrimethamine, weaning agents to eliminate the danger of addiction, e.g. nicotine for weaning off smoking, as well as bronchodilators such as formoterol.

The reservoir layer (b) particularly preferably contains nitroglycerine, scopolamine, formoterol, 17β-oestradiol, progesterone or combinations of 17β-oestradiol with norethisterone 17-acetate as active substances or combinations capable of permeation.

The said active substances can be present in the reservoir layer (b) in free form, e.g. as acids or as bases, or as pharmaceutically acceptable salt, e.g. as chloride, bromide, acetate, fumarate, maleate, succinate, lactate, etc.

The reservoir layer (b) can optionally contain further auxiliaries. Suitable auxiliaries are those such as water, isotonic aqueous sodium chloride solution, dextrose in water or sodium chloride solution, liquid glyceryl triesters with low molecular weight fatty acids, lower alkanols, natural oils such as corn oil, arachis oil, sesame oil, castor oil and the condensation products thereof with ethylene oxide and the like, hydrocarbons such as pharmaceutical grade mineral oil, silicones, emulsifiers, such as mono- or diglycerides of fatty acids, phosphatidic acid derivatives such as lecithin or cephalin, polyalkylene glycols, such as polyethylene glycol, aqueous phases to which a swelling agent has been added, such as sodium carboxymethylcellulose, sodium alginate, polyvinylpolypyrrolidone etc, to which it is also possible to add dispersing agents or emulsifiers such as lecithin, and the like. It is furthermore possible to add to these auxiliaries other additives such as preservatives, stabilizers, wetting agents etc.

The protective film (c) which can be pulled off the reservoir layer (b) is removed before application. It consists of materials which are impermeable to the constituents of the reservoir layer (b). It is possible to use for this the same materials which can serve to produce the covering layer (a) as well as metal foils, e.g. thin aluminum foil. Suitable surface treatment, e.g. silicone treatment, makes it possible to pull organic polymers off the adhesive layer (b).

The multilayer plaster according to the present invention preferably has the following constituents:

(a) a covering which is impermeable for the constituents of the reservoir layer (b), (b) a reservoir layer which is able to deliver active substance and which consists of optionally crosslinked butadiene/styrene block copolymers or ethylene/butadiene/styrene block polymers mixed with polyisobutylene with a molecular weight range of about $1.0 \times 10^3$ to $5.0 \times 10^4$ and contains at least one active substance which is able to permeate through the skin, at least one agent promoting the skin permeability of active substances and optionally further pharmaceutical auxiliaries and, (c) a protective film which can be pulled off the reservoir layer (b).

The invention primarily relates to a pharmaceutical plaster which has the following constituents:

(a) a covering layer which is impermeable for the constituents of the reservoir layer (b), (b) a reservoir layer which is able to deliver active substance and which consists of optionally crosslinked butadiene/styrene block copolymers or ethylene/butadiene/styrene block polymers mixed with polyisobutylene with a molecular weight range of about $1.0 \times 10^3$ to $5.0 \times 10^4$, and contains at least one active substance which is able to permeate through the skin and a combination of eucalyptol with N-methyl-2-pyrrolidone, and (c) a protective film which can be pulled off the reservoir layer (b).

The multilayer plaster according to the present invention is produced by applying to the protective film (c), which can be pulled off, the reservoir layer with its constituents and, thereto, the covering layer (a) or by reversing the procedure and applying to the covering layer (a) the reservoir layer (b) and, thereto, the protective film (c), and after one of the two process variants has been carried out the various layers are bonded together and the plaster is brought to the desired shape. This entails the plaster being stamped out. The reservoir layer (b) is optionally bonded to the covering layer (a) by use of additional adhesive. It is likewise possible for the various layers to be hot-welded.

The constituent of the reservoir layer (b) are mixed, before the multilayer plaster is produced, by, for example, converting the skin-penetrating agent, in particular the mixture of eucalyptol and N-methyl-2-pyrrolidone, with the block copolymer, e.g. a copolymer or terpolymer from the CARIFLEX or KRATON group, and the alkene homopolymer, e.g. a polyisobutylene from the OPPANOL group, into a homogeneous composition, especially by kneading, preferably at temperatures up to 100° C. The viscous composition can be rolled out after application to the covering layer (a), e.g. aluminized polyester film, or to the film (c) (release liner). The polymers can be crosslinked by irradiation with high-energy light, e.g. by UV light, e.g. with a mercury lamp as source, where appropriate using a suitable photoinitiator such as 2-hydroxy-2-methyl-1-phenylpropan-1-one (Darocur ® Merck) or 2,2-dimethoxy-1,2-diphenylethan-1-one (Irgacure ® 651, Ciba-Geigy). It is then possible to apply the active substance, optionally dissolved in a small amount of penetrating agent, to the crosslinked polymeric material. Alternatively, the active substance can be mixed with the polymeric material. For further saturation of the adhesive layer the latter can be left to swell with further penetrating agent or solution of the penetrating agent containing active substance for several hours to days.

The production processes and uses are described in U.S. Pat. Nos. 3,598,122, 3,598,123, 3,797,494 and 4,060,084, preferably in DE-A Nos. 2,604,718 and 3,205,258 or in U.S. Pat. Nos. 4,031,894 and 4,262,003 or in the publication Schweiz. Rundschau Med. (Praxis) 74, No. 11, 257–260 (1985) for the production of matrix or monolith systems, the use according to the invention not being confined to the transdermal therapeutic systems described in these publications.

EXAMPLE 1

(1a) 52 g of a mixture of 1,8-cineole with N-methyl-2-pyrrolidone (9 parts by weight of 1,8-cineole and 1 part by weight of N-methyl-2-pyrrolidone) are converted into a homogeneous composition with 33.6 g of styrene/butadiene block copolymer of the CARIFLEX TR 1107 type and 14.4 g of polyisobutylene with an average molecular weight of $4 \times 10^4$ of the OPPANOL B-10 type.

(1b) A 1 mm-thick metal frame with a rectangular opening ($3 \times 8$ cm) is placed on a covering film which is about 0.1 mm thick and is made of aluminized polyester (PE 3M Co. USA). 3.2 g of the formulation prepared as in (1a) are introduced into the opening of the metal frame and covered with a pull-off film made of siliconized polyester (DuPont). A Jauch type heatable laboratory press is used for compression, at a working temperature of about 70° C., to give a bonded laminate, the layers of the laminate being bonded together under a pressure of about 6 bar for about 30 sec. The sheet-like laminate is taken out of the frame, the release liner is removed, and the laminate is irradiated with UV light for 120 sec (Minicure Marck 2, Primarc Ltd.)

About 2% by weight of progesterone (based on the monolith mass) is applied by dissolving the progesterone in sufficient 1,8-cineole and N-methyl-pyrrolidone and spraying the solution onto the sheet. The laminate loaded with active substance is covered again with pull-off film which is pressed on, and transdermal systems are stamped out of the laminate in the form of plasters of suitable size, e.g. of diameter about 2.6 cm.

(c) To produce plasters with a particularly thin reservoir layer (less than 50 μm thick) the constituents of the adhesive layer are dissolved in heptane, and the solution is poured onto the covering layer of aluminized polyester in such a way that a monolith layer of the desired thickness results after the solvent has evaporated off. The remaining process steps are analogous.

EXAMPLE 2

(2a) A mixture of 39.9 parts by weight of the styrene/butadiene block copolymer CARIFLEX TR 1107 and 26.6 parts by weight of the polyisobutylene OPPANOL B-10 is mixed with a solution of 5 parts by weight of 17$\beta$-oestradiol in 2.85 parts by weight of N-methyl-2-pyrrolidone and 25.65 parts by weight of 1,8-cineole to give a homogeneous composition.

(2b) 3.2 g of this formulation are placed on a covering film in analogy to Example (1b), but without irradiation, provided with a pull-off film, compressed and stamped out to give transdermal systems in the form of plasters with a diameter of 2.6 cm. The dimensions and delivery properties of these systems are indicated in the table.

(2c) The monolith composition from Example (2a) is additionally mixed with two parts by weight of 2-hydroxy-2-methyl-1-phenylpropan-1-on (Darocur® 1173, Merck). As a modification of Example (1b), 3.2 g of this formulation are placed on a first pull-off film—instead of on a covering film—and covered with a second pull-off film. A laminate is produced by compression of which a round plaster is punched. The first pull-off film on one side is removed, the uncoated side is irradiated with UV light for 42 sec and this side is covered with covering film. After another compression the second pull-off film is removed. The other, uncoated side is in turn irradiated with UV light for 42 sec and this open side of the adhesive layer is again provided with pull-off film. Dimensions and delivery properties of these systems are indicated in the table.

(2d) The formulation of Example (2a) is mixed with 2-hydroxy-2-methyl-1-phenylpropan-1-one (2 parts by weight) and placed on a first pull-off film. A second pull-off film is used as closure. A laminate is formed by compression, and plasters are stamped out. Removal of the first pull-off film on one side is followed by irradiation with UV light for 42 sec. The irradiated side is again covered with pull-off film, the pull-off film on the unirradiated side is removed, and this side is also irradiated with UV light for 42 sec. Both pull-off films are again removed and then the monolith system is stored for 96 hours in a 5% strength (by weight) solution of 17$\beta$-oestradiol in N-methyl-2-pyrrolidone and 1,8-cineole (1:9 w/w). The swollen matrix formulation is subsequently coated with covering film and pull-off film. Dimensions and delivery properties of these systems are indicated in the table.

(2e) Transdermal therapeutic systems are produced with 17$\beta$-oestradiol in analogy to Example (2d), with both sides of the adhesive layer being irradiated with UV light for 67 sec. Dimensions and delivery properties of the systems are indicated in the table.

(2f) The permeation properties in vitro of the systems of Example (2b)–(2e) are determined by measurement of the cumulative permeation of the active substance 17$\beta$-oestradiol through pig epidermis as follows: the pull-off film is removed from the relevant system, and the exposed area of the adhesive layer is fixed on the pig epidermis by pressing on. The pig epidermis with plaster is mounted in a diffusion cell described by T. J. Franz (J. Invest. Dermatol. 64, 190 (1975)). Bovine serum albumin solution is used as acceptor. The content of 17$\beta$-oestradiol in the acceptor fluid is determined by HPLC. The measurements are reported in the table.

TABLE

| | Dimensions and permeation properties of monolith systems in vitro. | | | | |
|---|---|---|---|---|---|
| Example No. | Dimensions of monolith system | | | Cumulative permeation | |
| | Diameter [mm] | Thickness [mm] | Weight [mg] | after 24 hours [$\mu$g/cm$^2$] | after 48 hours [$\mu$g/cm$^2$] |
| 2b | 26 | 1 | 470 | 4.4 | 6.9 |
| 2c | 26 | 1 | 470 | 9.8 | 15.3 |
| 2d | 22/49[1] | 1/3[1] | 400/5600[1] | 67.4 | 116.2 |
| 2e | 22/48[1] | 1/2,5[1] | 400/4400[1] | 39.9 | 60.2 |

[1]after swelling

EXAMPLE 3

Monolith systems which are characterized by a content of about 0.2–0.5% formoterol in the adhesive layer are produced in analogy to Example (2d).

What is claimed is:

1. A transdermal therapeutic system in the form of a multilayer plaster with the following constituents:
   (a) a covering layer which is impermeable to the constituents of the reservoir layer (b);
   (b) a reservoir layer which is able to deliver active substance and which consists of optionally cross-linked block copolymer based on styrene, alkadienes and optionally alkenes mixed with adhesive polymers and is optionally provided with an additional adhesive membrane layer and contains at least one pharmaceutically active agent capable of skin permeation, a combination of 70% 1,8-cineole and N-methyl-2-pyrrolidone as agent promoting the skin-permeability of the pharmaceutically active agent and optionally further pharmaceutical auxiliaries, and
   (c) a protective film which can be pulled off the reservoir layer.

2. Transdermal therapeutic system according to claim 1, characterized in that the reservoir layer (b) contains a combination of eucalyptol with a content of at least 70% 1,8-cineole and N-methyl-2-pyrrolidone as additional skin-penetrating agent.

3. Transdermal therapeutic system according to claim 1, characterized in that the reservoir layer (b) contains a combination of chemically pure 1,8-cineole (purity greater than 99%) and N-methyl-2-pyrrolidone as additional skin-penetrating agent.

4. Transdermal therapeutic system according to claim 1, characterized in that the combination of 1,8-cineole and N-methyl-2-pyrrolidone contains about 5–9.5 parts by weight of 1,8-cineole and, correspondingly, about 5–0.5 parts by weight (based on 10) of N-methyl-2-pyrrolidone.

5. Transdermal therapeutic system according to claim 4, characterized in that the combination of 1,8-cineole and N-methyl-2-pyrrolidone contains about 9 parts by weight of 1,8-cineole and 1 part by weight of N-methyl-2-pyrrolidone.

6. Transdermal therapeutic system according to claim 1, characterized in that the reservoir layer (b) contains nitroglycerine, scopolamine, formoterol, 17$\beta$-oestradiol or progesterone or combinations of 17β-oestradiol with norethisterone 17-acetate as active substances which are able to permeate.

7. Transdermal therapeutic system according to claim 1, characterized in that the reservoir layer (b) consists of ethylene/butadiene/styrene block polymers or butadiene/styrene block copolymers, which are wholly or partially crosslinked by exposure to high-energy radiation and which are mixed with polyisobutylene with an average molecular weight of $1.0 \times 10^3$ to $5 \times 10^4$.

8. Transdermal therapeutic system according to claim 1 with the following constituents:
   (a) a covering which is impermeable for the constituents of the reservoir layer (b),
   (b) a reservoir layer which is able to deliver active substance and which consists of optionally crosslinked butadiene/styrene block copolymers or ethylene/butadiene/styrene block polymers mixed with polyisobutylene with a molecular weight range of about $1.0 \times 10^3$ to $5.0 \times 10^4$ and contains at least one active substance which is able to permeate through the skin, at least one agent promoting the skin permeability of active substances and optionally further pharmaceutical auxiliaries and,
   (c) a protective film which can be pulled off the reservoir layer (b).

9. Process for the production of a transdermal therapeutic system according to claim 1, characterized in that applied to the protective layer (c) which can be pulled off are the reservoir layer (b) with its constituents and, thereto, the covering layer (a), or the procedure is reversed and applied to the covering layer (a) are the reservoir layer (b) and, thereto, the protective film (c), and after one of the two process variants has been carried out, the layers are bonded together and the product is brought to the desired shape.

\* \* \* \* \*